United States Patent [19]

Bruzzese et al.

[11] 4,038,382

[45] July 26, 1977

[54] ALKYL ESTERS OF POLYENE ANTIBIOTICS

[75] Inventors: Tiberio Bruzzese; Rodolfo Ferrari, both of Milan, Italy

[73] Assignee: SPA-Societe Prodotti Antibiotici S.p.A., Italy

[21] Appl. No.: 630,888

[22] Filed: Nov. 11, 1975

Related U.S. Application Data

[62] Division of Ser. No. 381,563, July 23, 1973, Pat. No. 3,936,526.

[30] Foreign Application Priority Data

July 24, 1972  United Kingdom .............. 34497/72

[51] Int. Cl.² ........................................... H61K 35/00
[52] U.S. Cl. .................................... 424/117; 424/115; 424/120; 424/122

[58] Field of Search ................ 424/115, 117, 120, 122

[56] References Cited

PUBLICATIONS

Chemical Abstracts 73:35698t and 35699u (1970).
Chemical Abstracts 80:121291f (1974).

*Primary Examiner*—Jerome D. Goldberg
*Attorney, Agent, or Firm*—Wenderoth, Lind & Ponack

[57] ABSTRACT

The present invention provides a process for the preparation of alkyl esters of polyene antibiotics, wherein a polyene antibiotic is reacted with a diazoalkane in the presence of a basic substance.

The present invention also provides, as new materials, alkyl esters of polyene antibiotics in which the alkyl radical of the ester grouping contains 2 or more carbon atoms.

10 Claims, 5 Drawing Figures

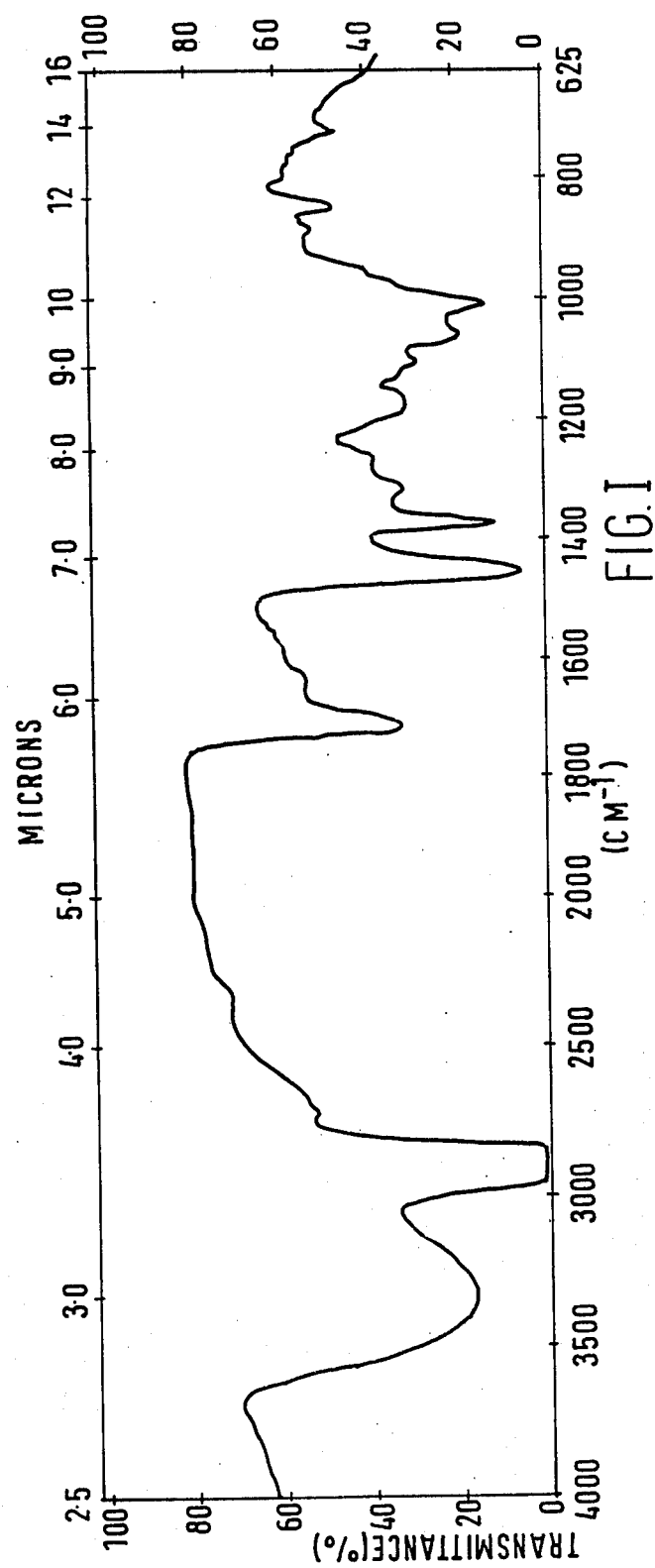
FIG. I

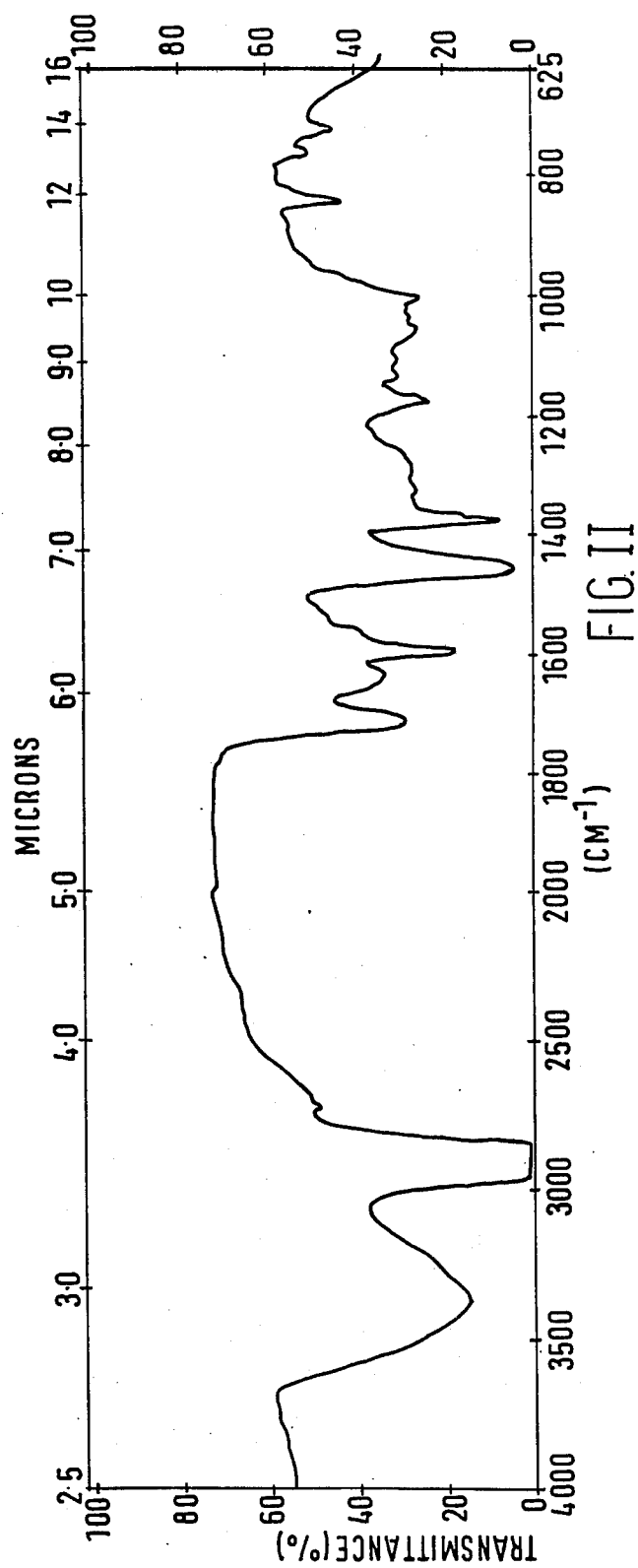
FIG. II

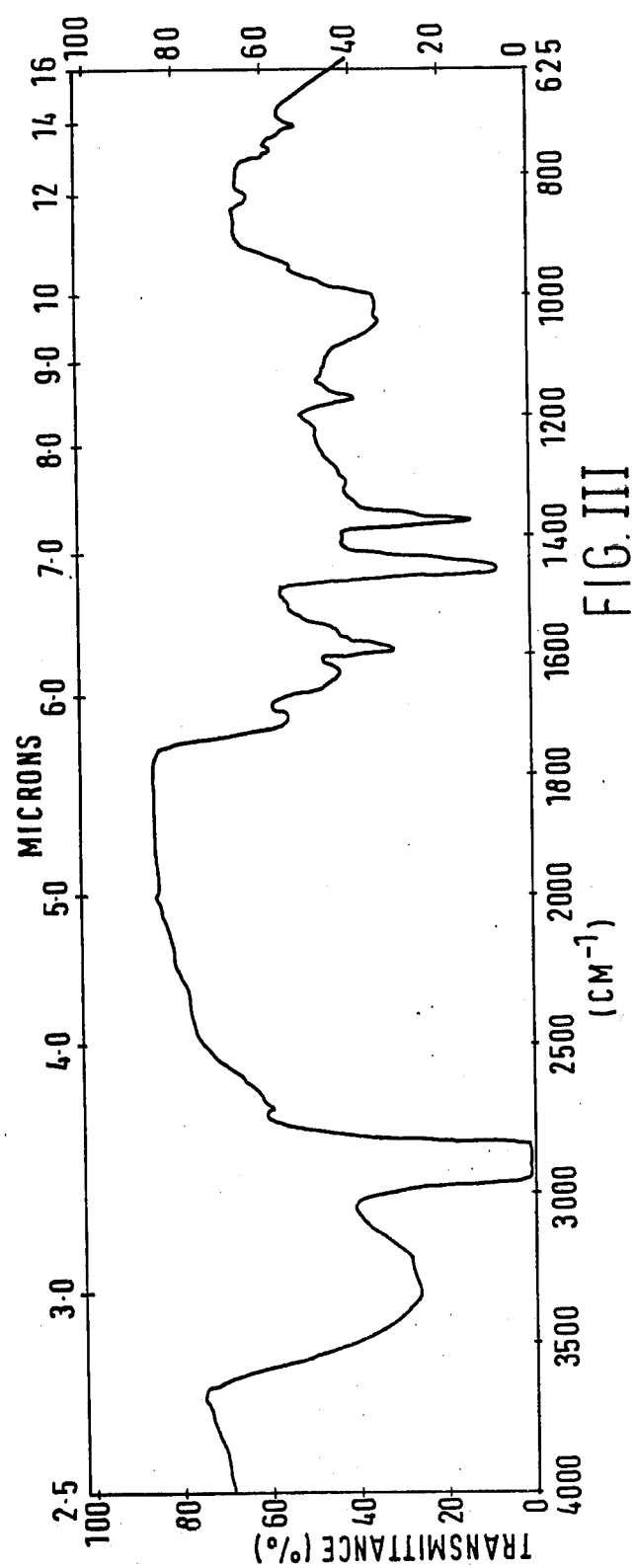
FIG. III

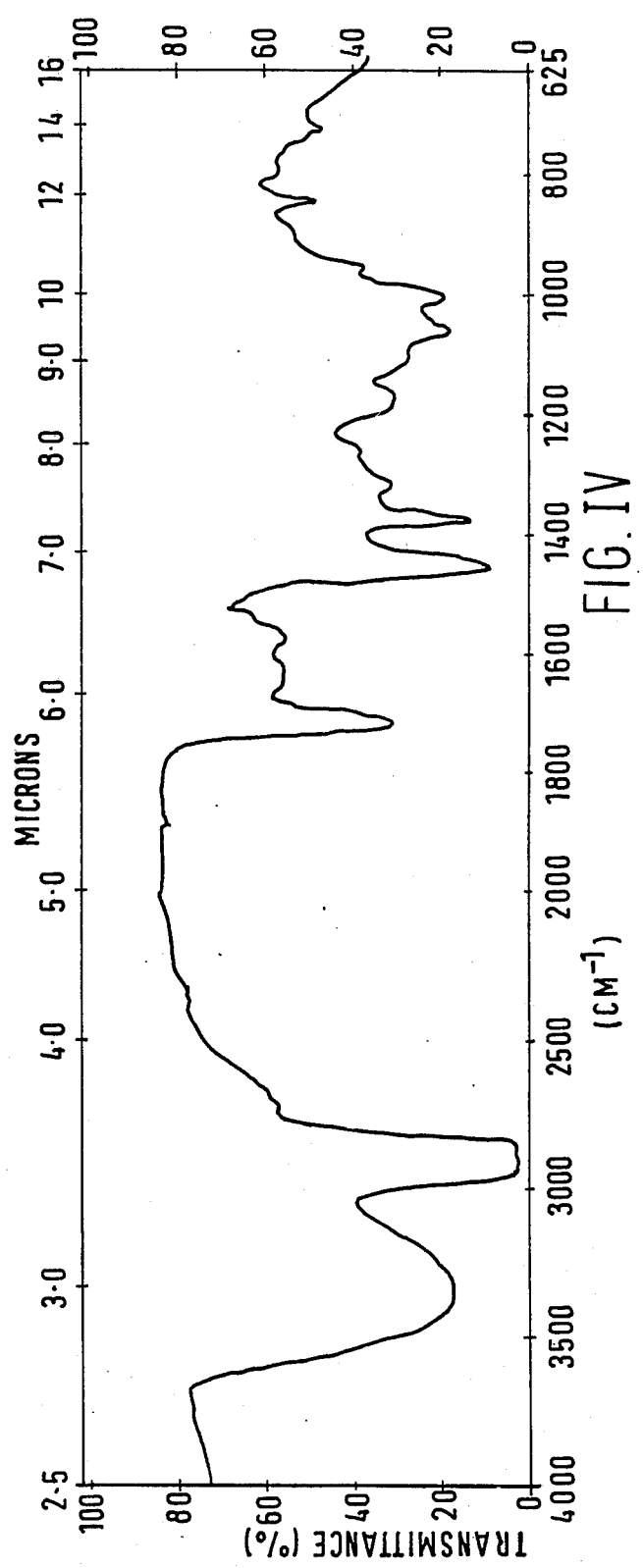
FIG. IV

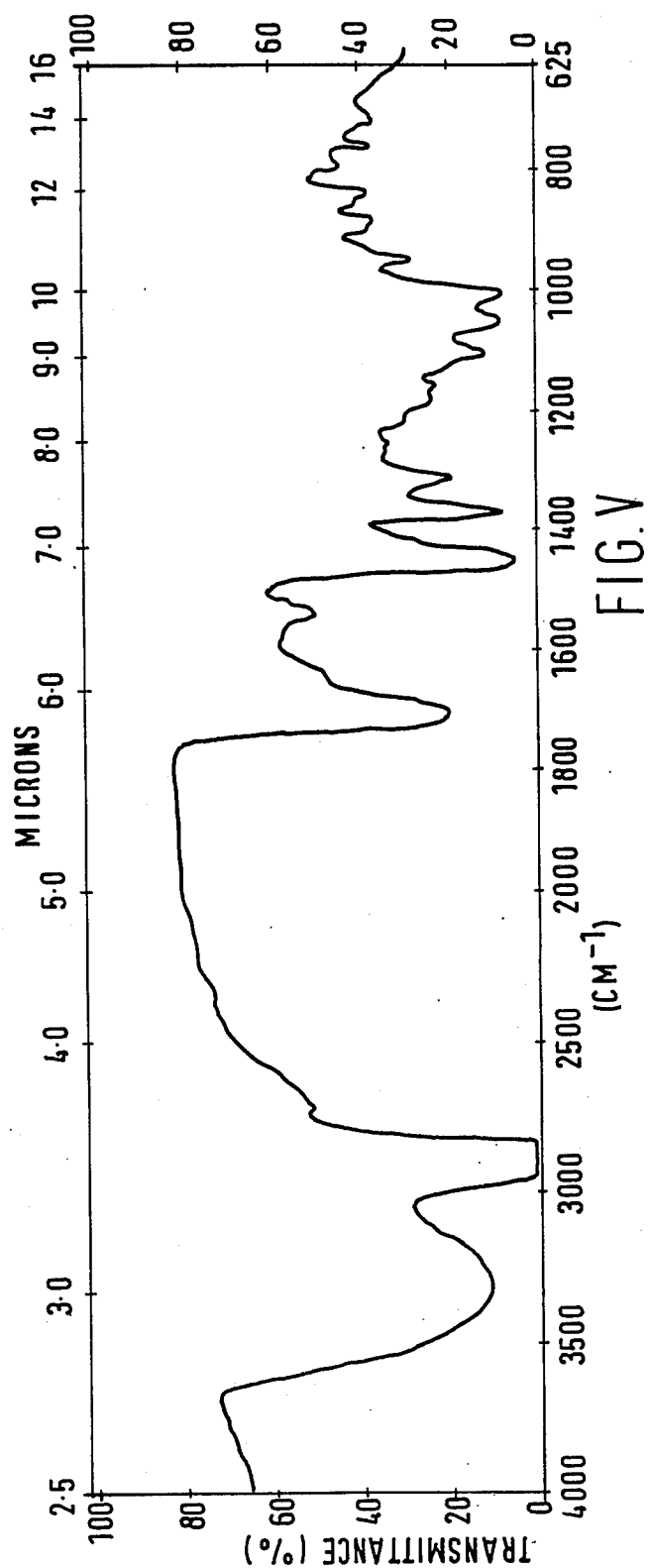
FIG. V

ALKYL ESTERS OF POLYENE ANTIBIOTICS

This is a Division of application Ser. No. 381,563, filed July 23, 1973, now U.S. Pat. No. 3,936,526.

BACKGROUND OF THE INVENTION

Polyene antibiotics have been known for a number of years. However, most of them have a low solubility in water which limits their use and, more important, they have a haemolytic action on red blood cells and are so toxic that their clinical use is either prevented or very restricted.

The polyene antibiotics constitute a wide category of substances which are normally produced by the metabolism of various microorganisms of the Streptomyces species. Having regard to their unsaturated structure containing conjugated double bonds they are divided into groups such as the hexaenes the pentaenes and, of particular importance, the heptaenes and the tetraenes, each group being characterised by its own ultra-violet absorption spectrum, which serves as an important means of structural elucidation.

Although the formulae of these substances are, in most cases, unknown or have only been partially elucidated, the substances are known to have a macrolide structure; as far as the physico-chemical characteristics are concerned, these substances are generally amphoteric; sometimes they are characterised by the presence of only one functional group, which may be acidic or basic.

Very few examples of esters of natural polyenic substances have been reported in the literature. As far as we know, the few such derivatives which have been reported are all methyl esters.

Consequently, there is clearly a great need for an improved method for preparing esters of the polyene antibiotics which have the same desirable properties as the natural antibiotic without suffering from the disadvantages thereof, such as toxicity and haemolytic activity.

Using the polyenic, amphoteric or acidic antibiotics as starting materials, we have found that the corresponding alkyl esters can readily be obtained therefrom. Detailed analytical investigations of the natural polyenes have shown that they often consist of a mixture of several substances with similar structures so it is obvious that they can be esterified as such as mixtures or separately, when the individual constituents are available.

SUMMARY OF THE INVENTION

Thus, according to the present invention, there is provided a process for the preparation of alkyl esters of polyene antibiotics, wherein a polyene antibiotic is reacted with an appropriate diazoalkane in the presence of a basic substance.

The esters thereby obtained, in which the alkyl radical of the ester grouping contains 2 or more carbon atoms, are new.

DETAILED DESCRIPTION OF THE INVENTION

The diazo compound is generally only used in slight excess in order to prevent the formation of products with a higher degree of alkylation, the diazoalkanes being used with the necessary degree of caution because they are poisonous and potentially explosive. The time of the reaction is generally between 1 and 24 hours and more often between 4 and 8 hours while the reaction temperature is generally kept at between 0° and 50° C., or, most advantageously, at about ambient temperature (15° – 30° C.).

When the evolution of nitrogen has ceased, which indicates that the reaction has terminated, the desired ester can be isolated, for example, by precipitation with an appropriate solvent and subsequent filtration; if desired, it can be recrystallised from appropriate solvents or purified by column chromatography.

The preferred solvents for the esterification reaction include dimethyl sulphoxide, dimethyl formamide, formamide, dimethyl acetamide 2-ethoxyethanol, pyridine and other organic solvents having a high dissolving action for the original polyenes and being, at the same time, inert to the diazolalkane used for the reaction; in contrast thereto, precipitating agents with a lowsolvent power are used for the recovery of the reaction product such agents including ether, benzene, water in excess and the like. The crude esters thereby isolated can be purified for analytical purposes by using appropriate mixtures of solvents, such as dimethyl sulphoxide/ether, dimethyl sulphoxide/water, dimethyl acetamide/water and the like.

Chromatographic purification is usually carried out on a column of silica gel, using more or less complex mixtures of solvents as eluents for example pyridine/petroleum ether or butanol/ethanol/acetone/ammonia.

As stated above, the esterification of the polyene antibiotics is carried out in the presence of a basic substance, such as ammonia which is added in stoichiometric to catalytic quantities. Organic bases, for example triethylamine, can also be used.

Carrying out the reaction at an alkaline pH (for example pH 10 – 10.5, determined after appropriate dilution up to 1%) prevents the formation of certain by-products. some of which are unknown, and, therefore, the products obtained are very pure and have a high microbiological activity.

The alkyl esters according to the present invention are crystalline solids with a slight yellow to brown colour, the melting points of which cannot be well determined. They are usually insoluble in water and in aqueous solutions of alkalis (absence of acid functions) and also in ether, petroleum ether, benzene and the like; sparingly soluble or insoluble in alcohols and in anhydrous acetone; but moderately soluble when these solvents contain 10 – 20% of water. However, they are very soluble in dimethyl sulphoxide, pyridine, formamide and dimethyl-acetamide. It is interesting to observe that several of them are able to form complexes in varying weight ratios with particular substances, for example with sodium desoxycholate, sodium lauryl sulphate and others which have been reported in literature for the natural polyenes, these complexes giving aqueous solutions in which the substances are finely dispersed in colloidal form (pseudosolutions). This behaviour shows that the carboxyl group of the polyenes is not indispensable for the formation of these molecular complexes.

The alkyl esters according to the present invention contain the unaltered polyenic structure of the starting substances, as is demonstrated by their ultra-violet absorption spectra which are entirely unchanged with regard to the wavelengths of the absorption maxima and show only very slight changes in the intensity values, as is to be expected. Occasional marked modifications found in the ratios between the intensities of the various maxima in comparison with the natural substance have, in contrast, shown a certain degradation of the substance, with consequent diminution of the microbiological activity. Because they are substances with a high molecular weight, the percentage elementary analysis is not markedly changed by the substituent introduced and often the elementary analysis cannot provide structural elucidation. However, the method and the reagents used in the reaction, in agreement with the general procedures found in literature, indicate that the new compounds have the structure of alkyl esters. This is supported by the disappearance of the acid function from the starting material (insolubility in alkali) and by the infra-red spectrum which shows a strong absorption band with frequencies generally over 1700 cm$^{-1}$ attributable to the stretching vibration of the C=0 group of an ester. The NMR spectra (solutions in dimethyl-d$_6$sulphoxide) are also of value and have characteristic peaks which, in the case of the methyl esters, show a chemical shift, compared with tetramethyl-silane, of about 3.5 ppm. The purity of the productobtained, in particular the total disappearance of the starting polyenes, is easily checked by means of thin layer chromatography on silica gel F254. With this technique and using solvent systems of the type butanol/ethanol/acetone/concentrated aqueous ammonium hydroxide solution (2:5:1:3), all the polyenic esters examined show Rf values which are much higher than those of the untreated substance and thus provide an effective control of the purity. The spots can be seen by exposure to ultra-violet light at appropriate wavelength.

With regard to their microbiological activitiy, the alkyl esters according to the present invention possess substantially the same spectrum of action as the natural polyene: they have little or no activity against gram positive and gram negative bacteria but are active against numerous species of pathogenic fungi, especially *Candida albicans*, as well as against yeasts are protozoa. When the original substance also has an activity against certain protozoa, as is often the case, especially against *Trichomonas*, this activity is usually also retained. The degree of action of these esters is strictly connected with that of the starting substances, so that it cannot be taken as a whole for the entire class of substances, although it has been shown that the heptaene esters examined inhibit the growth of the same strain of *Candida albicans* at the same concentration or at 2 - 4 or more times lower concentration, i.e, the activity is the same or better. The tetraene esters, on the other hand, are usually just as active although their action is sometimes considerably reduced, even though it loses none of its theoretical and practical value.

The toxicity of the alkyl esters is quite low and, in any case, markedly lower than that of the starting compounds. The tests were carried out by administering suspensions in carboxymethylcellulose to various experimental animals by the oral and peritoneal routes. The potential toxicity of the polyenes is influenced to a considerable extent by their very low solubility in water and in physiological media. Since this greatly affects the possibility of absorption, other tests have been carried out, after solubilisation of the compounds with bile acids, to avoid changes in the solubility producing misleading results. In this case, too, there was a considerable increase in the LD$_{50}$ values for the new esterified derivatives. The haemolytic action, a side-effect which has greatly reduced the possibilities of using the heptaenic polyenes clinically, is markedly decreased in the new derivatives which have a minimum haemolytic concentration which is up to 10 - 20 times higher than that of the starting materials.

Seen as a whole, the microbiological and toxicological properties of the alkyl esters and, in particular, of the alkyl esters of the heptaenes, show their great importance as therapeutic agents for combating fungal and protozoal infections in humans, animals and plants.

Of particular interest is their use in the field of dermatological infections caused by *Candida albicans* and by *Trichomonas vaginalis,* either in the form of an ointment, cream, foam and tincture for topical use or in the form of vaginal suppositories. The low absorption through the intestinal wall of most of the insoluble derivatives indicates them particularly for combating, by oral administation, the intestinal mycotic infections which often arise in humans after prolonged treatments with antibacterial agents, such as chloroamphenicol and tetracycline. However, the possibility of being able to add the polyenic esters to vehicles consisting of the most varied organic and non-toxic solvents, together with their capacity of forming water-soluble or colloidally dispersible molecular complexes with numerous substances, such as the bile acids, does not preclude their possibility of absorption after oral and parenteral administration and their consequent effectiveness in combating generalised infections. Preliminary clinical investigations have been successfully carried out on some of the alkyl esters, for example amphotericin methyl ester. The following Examples are given for the purpose of illustrating the present invention.

EXAMPLE 1

10 g. of amphotericin B are dissolved in 100 ml. dimethyl sulphoxide, whereafter a solution of ammonium hydroxide is added dropwise, while stirring, in a quantity sufficient to bring the pH of the solution to about 10, the pH value being measured on a sample of solution after dilution to 1% by adding a mixture of dimethyl sulphoxide/water (1:1). 100 ml. of a 2.5% ethereal solution of diazomethane are then added cautiously and the reaction mixture is kept at ambient temperature, while slowly stirring, for 6 hours. After this time, the reaction product is precipitated by the addition of excess ether and the precipitate is collected by filtration. After treatment with a mixture of acetone/ether and subsequent thorough washing with water, the desired amphotericin B methyl ester is obtained in the form of a yellow crystalline solid. Thin layer chromatographic analysis on plates of silica gel F254, using a mixture of butanol/ethanol/acetone/concentrated aqueous ammonium hydroxide solution (2:5:1:3) as eluent system, shows a single spot with an Rf value around 0.74 (amphotericin B, Rf 0.41 ). The ultra-violet absorption spectrum in ethanolic solution shows maxima at 346, 364, 383 and 407 m$\mu$, as does the starting material, while the infra-red spectrum in nujol suspension (see FIG. I of the accompanying drawings) shows an absorption band at 1713 cm$^{-1}$, attributable to the stretching vibration of a C=0 ester group.

Amphotericin B methyl ester inhibits the growth of a strain of *Candida albicans* (minimum inhibiting concentration) at a dilution of 0.3 mcg./ml. (Amphotericin B, MIC 0.6 mcg./ml.) and has a minimum haemolytic concentration on rat erythrocytes after 1 hour at 25 - 50 mcg./ml. (Amphotericin B, MHC 2.25 mcg./ml.). Acute toxicity tests, after intravenous administration to mice or suspensions of the product in amorphous form (isolated from dimethyl sulphoxide-water) give $LD_{50}$ values of about 60 mg./kg. (Amphotericin B under the same experimental conditions $LD_{50}$ about 5 mg./kg.). When used in crystalline form, the ester has a very low toxicity by the oral and peritoneal routes in various experimental animals, as has the natural polyene.

EXAMPLE 2

5 g. of crystalline amphotericin B methyl ester obtained by the procedure described in Example 1, are dissolved in 100 ml. dimethyl sulphoxide. The solution obtained is added, while stirring, at ambient temperature to 500 ml. of a 0.5 % solution of sodium desoxycholate, an amorphous precipitate thereby being obtained. This material is isolated by centrifuging and washed first with a 0.5% solution of sodium chloride and then thoroughly with distilled water.

The product is again isolated by centrifuging and then suspended in a solution containing 4.2 g. sodium desoxycholate in 300 ml. distilled water and the mixture is kept at ambient temperature for 18 hours, with occasional stirring.

The amphotericin B methyl ester dissolves gradually and finally the solution obtained is filtered to remove traces of suspended material, whereafter the filtrate is evaporated to dryness by lyophilisation or by careful distillation in a vacuum. The solid obtained is stable and readily soluble in water; microbiologial examination and spectrophotometric titration demonstrate that it contains amphotericin B methyl ester in percentages generally above 50% (about 50 – 60%) and that its microbiological activity is fully retained. Acute toxicity tests carried out on this water-soluble compound with sodium desoxycholate give $LD_{50}$ values of about 80 mg./kg. (expressed as amphotericin D methyl ester) after intravenous administration to mice (amphotericin B complex with sodium desoxycholate: $LD_{50}$ about 4 mg./kg.).

EXAMPLE 3

To a solution of 2 g. amphotericin B in 40 ml. dimethyl sulphoxide, containing an aqueous ammonium hydroxide solution as in Example 1, are added dropwise 40 ml. of a 1% ethereal solution of diazobutane. The reaction mixture is slowly stirred at 25° C. for 8 hours and then excess ether is added, a yellow crystalline product being obtained, which is isolated by filtration, washed well with ether and then with water and dried in a vacuum at ambient temperature, amphotericin B butyl ester being obtained in high yields. The physicochemical analysis of the compound gives values which do not differ very much from those of the corresponding methyl ester: the Rf value on silica gel in thin layer chromatography is about 0.77, while, in the infra-red spectrum, the absorption band of the carbonyl group seems to be at a slightly lower frequency (1709 $cm^{-1}$).

The amphotericin B butyl ester has a minimum inhibiting concentration on *Candida albicans* of about 1.2 mcg./ml. and a minimum haemolytic concentration on rat erythrocytes, after a 1 hour experiment, of about 50 mcg./ml.

The product can be solubilized by using sodium desoxycholate in the manner described in Example 3. The compound obtained retains the microbiological activity of amphotericin B butyl ester and forms a stable pseudosolution in an aqueous medium.

EXAMPLE 4

5 g. ayfactin are dissolved in 50 ml. dimethyl sulphoxide and a small quantity of aqueous ammonium hydroxide is added thereto until the pH is about 10, this value being measured after dilution to 1% with dimethyl sulphoxide/water (1:1), whereafer 40 ml. of a 2.5% ethereal solution of diazomethane are added dropwise, while stirring slowly.

After working up the reaction mixture as in Example 1, there is obtained a quantitative yield of ayfactin methyl ester in the form of a yellow to yellow-brown crystalline solid. The product has an Rf value of about 0.75 by thin layer chromatography on silica gel, using the usual solvent mixture butanol/ethanol/acetone/concentrated aqueous ammonium hydroxide solution (2:5:1:3) (ayfactin, Rf about 0.48).

The ultra-violet spectrumin pyridine solution gives maxima absorption values at 346, 366, 388 and 410 m$\mu$, as does the natural polyene, and the infra-red spectrum (see FIG. II of the accompanying drawings) has an absorption peak of the ester C=O group at about 1715 $cm^{-1}$.

Ayfactin methyl ester has a minimum inhibiting concentration value on *Candida albicans* of 0.3 – 0.6 mcg./ml., which is about the same as that of the original ayfactin. The product is also active against *Trichomonas vaginalis*. The toxicity tests show an $LD_{50}$ of over 1000 mg./kg. by the oral route and of about 30 mg./kg. after administration in suspension to mice by the peritoneal route (ayfactin, $LD_{50}$ about 1 mg./kg. i.p.).

Esters with similar chemical and biological properties are also obtained by using the single components ayfactin A and ayfactin B as starting materials.

EXAMPLE 5

A solution of 20 g. candicidin in dimethyl sulphoxide is treated with an ethereal solution of diaxomethane in the presence of aqueous ammonium hydroxide solution as in Example 1. The same procedure is as in Example 1, high yields of candida methyl ester being obtained in the form of a dark yellow, crystalline powder. The product is characterised by thin layer chromatography with the usual techniques and has an Rf value of about 0.77 (candicidin, Rf 0.48); ultra-violet absorption maxima in ethanolic solution at 340, 359, 378 and 400 m$\mu$ as for candicidin; infra-red absorption band (see FIG. III of the accompanying drawings) of the ester carbonyl at about 1710 $cm^{-1}$. Candicidin methyl ester has a minimum inhibiting concentration on *Candida albicans* of 0.15 – 0.30 mcg/ml (candicidin, MIC 0.15 mcg/ml) and a minimum haemolytic concentration on rat erythrocytes, after 1 hour, of 5 – 10 mcg/ml (candicidin, MHC 0.3 – 0.6 mcg/ml). The acute toxicity, after peritoneal administration to mice of suspensions in carboxymethylcellulose, gives $LD_{50}$ values of about 15 mg/kg (candicidin $LD_{50}$, about 4 mg/kg).

EXAMPLE 6

10 g. nystatin, dissolved in 100 ml. dimethyl sulphoxide, are cautiously treated with 80 ml. of a 2% ethereal solution of diazomethane in the presence of aqueous ammonium hydroxide solution as in Example 1. The reaction mixture is slowly stirred for 4 hours at 25° C. and then excess ether is added to precipitate the reaction product. The solid is filtered off and washed with ether and then with water to give the desired product in the form of a light yellow, crystalline solid. The nystatin methyl ester obtained has an Rf value of 0.68 (nystatin, Rf 0.39) by thin layer chromatography on silica gel, eluating with butanol/ethanol/acetone/concentrated aqueous ammonium hydroxide solution (2.5:1:3). It shows absorption maxima in the ultra-violet spectrum, carried out in ethanol solution, at 292, 304 and 319 m$\mu$, which are the same frequencies as for nystatin, and a peak attributed to the C=0 stretching of an ester at 1718 cm$^{-1}$ in the infra-red spectrum (see FIG. IV of the accompanying drawings). Microbiologically, nystatin methyl ester inhibits the growth of *Candida albicans* at 12 mcg/ml (nystatin, MIC 6 mcg/ml).

EXAMPLE 7

2 g. pimaricin in dimethyl sulphoxide solution are treated with diazomethane in the presence of aqueous ammonium hydroxide solution in the manner described in Example 1. The methyl ester of pimaricin thereby obtained has an Rf value, carrying out the chromatography in the usual way, of about 0.74 (pimaricin, Rf 0.42). The UV spectrum in ethanolic solution has absorption maxima at 290, 303 and 318 m$\mu$ as does the original pimaricin, and has a strong band around 1710 cm$^{-1}$ in the infra-red spectrum (see FIG. V of the accompanying drawings). The product is only moderately active against *Candida albicans* having a minimum inhibiting concentration of over 40 mcg/ml (pimaricin, MIC 8 – 10 mcg/ml) and has little or no haemolytic activity on rat erythrocytes.

EXAMPLE 8

To a solution of 2 g. of the heptaene antibiotic DJ-400 in 40 ml. dimethyl sulphoxide is added a concentrated solution of ammonium hydroxide in a quantity sufficient to bring the pH of the solution to about 10 (the pH value is measured after dilution to 1% by adding a mixture of dimethyl sulphoxide/water (1:1)). 20 ml. of a 2.5% ethereal solution of diazomethane are then added, while slowly stirring, whereafter the reaction mixture is kept at ambient temperature for 2 hours. The reaction mixture is then filtered and excess water is added, the methyl ester of antibiotic DJ-400 being obtained; it is isolated by filtration, washed well with water and acetone and dried in a vacuum. The DJ-400 methyl ester is a yellow crystalline product.

Thin layer chromatographic analysis on silica gel, using the usual solvent system, shows an Rf value of about 0.77, which is higher than the Rf value of the starting antibiotic DJ-400. The ultra-violet absorption spectrum in ethanolic solution is practically unchanged and shows maxima at 402, 381, 360 and 340 m$\mu$, while the infra-red spectrum in nujol suspension shows a new absorption band sttributable to the stretching vibration of a C=0 ester group.

From the microbiological point of view, the methyl ester of antibiotic DJ-400 shows a marked activity against *Candida albicans* and *Trichomonas vaginalis*.

EXAMPLE 9

3 g. of antibiotic DJ-400 are dissolved in 60 ml. dimethyl sulphoxide and the solution so obtained is treated with ammonium hydroxide and then with ethereal solution of diazopropane as described in Example 8. After the usual working up, the propyl ester of antibiotic DJ-400 is obtained.

The product is identified by its infra-red spectrum and is characterized by thin layer chromatography (Rf = about 0.80); in the same way as the other alkyl esters, the propyl ester of antibiotic DJ-400 shows a strong activity against *Candida albicans* and *Trichomonas vaginalis*.

The present invention also provides pharmaceutical compositions, which can be administered orally or parenterally, containing at least one alkyl ester of a polyene antibiotic, in admixture with a solid or liquid pharmaceutical carrier.

The esters can be used in the pharmaceutical compositions as such or in the form of the previously mentioned soluble or dispersable complexes or in the form of acid-addition salts, especially the hydrochlorides.

Solid compositions for oral, rectal or vaginal administration include compressed tablets, effervescent tablets, pills, dispersable powders, capsules, granules and suppositories. In such solid compositions, the active material is admixed with at least one inert diluent, such as calcium carbonate, starch, alginic acid or actose. The compositions may also comprise, as is normal practice additional substances other than inert diluents for example, lubricating agents, such as magn esium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents and sweetening and flavouring agents.

The compositions according to the present invention, for oral administration, include capsules of absorbable material, such as gelatine, containing the active material, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilized, for example, by filtration through bacteria retaining filters, by incorporation into the compositions of sterilising agents, by irradiation or by heating. They may also be produced in the form of sterile solid compositions, which can be dissolved in sterile water or some other sterile injectable medium immediately before use.

The percentage of active ingredient in the compositions of the present invention may be varied, it being necessary that it should constitute a proportion such that a suitable dosage for the desired therapeutic effect shall be obtained.

Examples of pharmaceutical compositions containing the polyene antibiotic include the following:

EXAMPLE 10

Ointment

| Composition: | |
|---|---|
| amphotericin B butyl ester | 0.5 g. |
| alcoholic fats | 60 g. |
| lanolin | 15 g. |
| polyethylene glycol 1540 monostearate ad | 100 g. |

EXAMPLE 11

Liniment

| Composition: | |
|---|---|
| ayfactin methyl ester | 0.5 g. |
| dimethylacetamide | 5 g. |
| anhydrous lanolin | 15 g. |
| cetyl alcohol | 30 g. |
| oleyl alcohol | 15 g. |
| sorbitan trioleate | 10 g. |
| polyethylene glycol 1540 monostearate | 24 g. |

EXAMPLE 12

Vaginal suppositories

| Each vaginal suppository contains: | |
|---|---|
| antibiotic DJ-400 methyl ester | 5 mg. |
| dimethyl acetamide | 50 mg. |
| polyethylene glycol 1540 monostearate | 1.35 g. |
| cetyl alcohol | 0.500 g. |

EXAMPLE 13

Vaginal supporitories

| Each vaginal suppository contains: | |
|---|---|
| antibiotic DJ-400 propyl ester | 25 mg. |
| dimethyl acetamide | 50 mg. |
| polyethylene glycol 1540 monostearate | 1.35 g. |
| cetyl alcohol | 0.500 g. |

The pharmaceutical compositions illustrated in Examples 10 to 13 above show valuable anti-fungal and anti-protozoal activity when administered to humans.

We claim:

1. A process for the preparation of the methyl ester of ayfactin which comprises reacting ayfactin with diazomethane in the presence of a basic substance selected from the group consisting of ammonia, triethylamine and pyridine in a substantially stoichiometric quantity, the resulting pH being 10 to 10.5 (determined after dilution to 1%), the reaction being carried out at a temperature between 15° and 30° C.

2. The product of the process of claim 1.

3. A process for the preparation of the methyl ester of candicidin which comprises reacting candicidin with diazomethane in the presence of a basic substance selected from the group consisting of ammonia, triethylamine and pyridine in a substantially stoichiometric quantity, the resulting pH being 10 to 10.5 (determined after dilution to 1%), the reaction being carried out at a temperature between 15° and 30° C.

4. The product of the process of claim 3.

5. A process for the preparation of the methyl ester of nystatin, which comprises reacting nystatin with diazomethane in the presence of a basic substance selected from the group consisting of ammonia, triethylamine and pyridine in a substantially stoichiometric quantity, the resulting pH being 10 to 10.5 (determined after dilution to 1%), the reaction being carried out at a temperature between 15° and 30° C.

6. The product of the process of claim 5.

7. A process for the preparation of the methyl ester of pimaricin which comprises reacting pimaricin with diazomethane in the presence of a basic substance selected from the group consisting of ammonia, triethylamine and pyridine in a substantially stoichiometric quantity, the resulting pH being 10 to 10.5 (determined after dilution to 1%), the reaction being carried out at a temperature between 15° and 30° C.

8. The product of the process of claim 7.

9. A process for the preparation of the methyl ester of the heptaene antibiotic DJ-400 which comprises reacting heptaene antibiotic DJ-400 with diazomethane in the presence of a basic substance selected from the group consisting of ammonia, triethylamine and pyridine in a substantially stoichiometric quantity, the resulting pH being 10 to 10.5 (determined after dilution to 1%), the reaction being carried out at a temperature between 15° and 30° C.

10. The product of the process of claim 9.

* * * * *